(12) United States Patent
Yoon et al.

(10) Patent No.: US 6,325,794 B1
(45) Date of Patent: Dec. 4, 2001

(54) LASER HANDPIECE

(75) Inventors: Gil-won Yoon, Suwon; Hong-sig Kim, Seoul; Tae-min Hong, Seoul; Sang-cheol Lee, Seoul, all of (KR); Alexander Zabaznov; Alexander Ianukovitch, both of Minsk (BY)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 09/310,733

(22) Filed: May 13, 1999

(30) Foreign Application Priority Data

May 13, 1998 (KR) ................................. 98-17187
Apr. 27, 1999 (KR) ................................. 99-15027

(51) Int. Cl.[7] .................................................... A61B 18/18
(52) U.S. Cl. ............................... 606/17; 606/16; 606/18
(58) Field of Search .......................... 606/2, 4, 10, 13, 606/16–19; 433/29–31; 607/88, 89, 90, 93

(56) References Cited

U.S. PATENT DOCUMENTS

| | | | |
|---|---|---|---|
| 4,459,986 | * | 7/1984 | Karaki . |
| 4,608,980 | * | 9/1986 | Aihara . |
| 4,849,859 | * | 7/1989 | Nagasaw . |
| 5,388,987 | * | 2/1995 | Badoz et al. . |
| 5,388,988 | * | 2/1995 | Goisser et al. . |
| 5,397,327 | | 3/1995 | Koop et al. . |
| 5,458,594 | * | 10/1995 | Mueller et al. . |
| 5,616,141 | | 4/1997 | Cipolla . |
| 5,833,684 | * | 11/1998 | Franetzki . |
| 5,999,687 | * | 12/1999 | Abraham et al. . |

* cited by examiner

*Primary Examiner*—Linda C. M. Dvorak
*Assistant Examiner*—Roy Gibson
(74) *Attorney, Agent, or Firm*—Burns, Doane, Swecker & Mathis

(57) ABSTRACT

A laser handpiece using an optical system such as a prism. The laser handpiece includes a laser fiber for irradiating laser beam output from a laser generating device, a first beam path changing portion for changing a traveling path of the laser beam output from the laser fiber, a second beam path changing portion for changing finally the traveling path of the laser beam output from the first beam path changing portion, a focus lens for focusing the laser beam output from the second beam path changing portion onto a point, and a main body for containing the laser fiber, the first beam path changing portion, the second beam path changing portion and the focus lens. Thus, an optical axis can be easily aligned and the traveling path of the laser beam can be easily changed within a small space, so the laser handpiece can be manufactured in a convenient shape for use.

20 Claims, 5 Drawing Sheets

LASER HANDPIECE

BACKGROUND OF THE INVENTION

1. Field of the Invention

The present invention relates to a laser handpiece, and more particularly, to a laser handpiece for irradiating the output of a laser generating device onto a predetermined position.

2. Description of the Related Art

In general, a laser handpiece is for accurately irradiating the output of a laser generating device onto a specific target with the hands. In particular, a laser handpiece as medical devices is used for surgical purposes, such as cutting and coagulating affected parts of a patient by irradiating laser beam thereon.

Laser beams having a wavelength of 1.06 $\mu$m or 1.32 $\mu$m have been used to operate on soft tissue such as the gums or the skin, other than firm parts such as bones or teeth, and usually a laser fiber of silica is inserted into the laser handpiece it for such purpose. In this case, the laser fiber is installed through the entire length of the laser handpiece such that the laser beam generated at one end of the laser fiber is directly irradiated onto the affected part of a patent.

Meanwhile, a laser beam having a wavelength of 2.94 $\mu$m is used to operate firm parts such as teeth or bone, and a laser handpiece for such purpose adopts a laser fiber of sapphire. This is because the general laser fiber of silica cannot normally transmit a laser beam having a wavelength of 2 $\mu$m or longer due to its high loss ratio during the transmission.

FIG. 1 shows a conventional laser handpiece used for surgical operation on the teeth or the bone.

The conventional laser handpiece shown in FIG. 1 comprises in a main body 10 a laser fiber of sapphire for irradiating a laser beam output from a laser generating device (not shown), a collimating lens 14 for collimating the laser beam irradiated by the laser fiber 12, a reflective mirror 16 for changing a traveling path of the laser beam output through the collimating lens 14, and a focus lens 18 for focusing the laser beam reflected by the reflective mirror 18.

In the conventional laser handpiece, the traveling path of the laser beam irradiated from the laser fiber 12 is changed using the reflective mirror 16 because the laser fiber 12 of sapphire does not bend much due to its poor flexibility. The reason for changing the traveling path of the laser beam is to allow a user to work more easily with the device.

However, the conventional laser handpiece in FIG. 1 has a straight handle in the main body 10, so it is inconvenient for the user to use the laser handpiece.

In general, the angle of the handle with respect to the main body of the laser handpiece for the convenience grip is in a range between 12° and 140°, and for such a design the traveling path of the laser beam must be changed two or more times using two or more reflective mirrors. Changing the traveling path of the laser beam using a reflective mirror gives rise to an aberration. As a result, there is a problem in that the laser beam cannot be irradiated onto one point. Also, changing the traveling path of the laser beam using a reflective mirror increases the size of the reflective mirror because the laser beam strikes the reflective mirror at a predetermined angle. Also, it is difficult to accurately tilt the reflective mirror. As a result, the size of the main body of the hand piece increases, so that there is a problem in that griping the hand piece while working with the instrument is difficult.

SUMMARY OF THE INVENTION

It is an object of the present invention to provide a laser handpiece in which a traveling path of laser beam can be easily changed in a small space, so that it is easy for a user to grip the same while working with the instrument.

To achieve the object, there is provided a laser handpiece comprising: a laser fiber for irradiating laser beam output from a laser generating device; a first beam path changing portion for changing a traveling path of the laser beam output from the laser fiber; a second beam path changing portion for changing finally the traveling path of the laser beam output from the first beam path changing portion; a focus lens for focusing the laser beam output from the second beam path changing portion onto a point; and a main body for containing the laser fiber, the first beam path changing portion, the second beam path changing portion and the focus lens.

Preferably, the first beam path changing portion comprises: a collimating lens for collimating the laser beam irradiated from the laser fiber; and one or more prisms for changing the traveling path of the laser beam output from the collimating lens.

Preferably, the second beam path changing portion comprises a reflective mirror for finally changing the traveling path of the incident laser beam and outputting the reflected beam to the focus lens.

Preferably, the prism of the first beam path changing portion is a Dove prism having two refractive planes and two parallel reflective planes.

Preferably, the main body is bent at an angle of 90° or over for convenience of use.

Preferably, the laser handpiece further comprises: air and water supply tubes for supplying air and water from the outside to clean and cool an irradiated portion being irradiated by the laser beam; and a light irradiating tip having an injecting portion for injecting the air and water supplied via the air and water supply tubes into the irradiated portion, and an energy transferring portion for transferring the energy of the laser beam condensed by the focus lens to the irradiated portion.

Preferably, the energy transferring portion is an optical fiber.

Preferably, the light irradiating tip further comprises: a connecting portion to be connected to the main body; and a protecting portion for protecting the energy transferring portion from damage by a physical force.

Preferably, an end part of the energy transferring portion and an end part of the protecting portion end at the same end position.

Preferably, an end part of the energy transferring portion is recessed compared to an end part of the protecting portion.

Preferably, an end part of the energy transferring portion is formed to protrude compared to an end part of the protecting portion.

Preferably, the protecting portion further comprises one or more injecting holes at the end part, for injecting the air and water into the irradiated portion.

Preferably, the first beam path changing portion is formed by bending the laser fiber for irradiating the laser beam output from the laser generating device at a predetermined angle such that an end part of the laser fiber irradiating the laser beam is located near the second beam path changing portion, and the second beam path changing portion comprises a concave reflective mirror for changing the traveling path of the laser beam output from the laser fiber toward the focus lens.

BRIEF DESCRIPTION OF THE DRAWINGS

The above object and advantages of the present invention will become more apparent by describing in detail preferred embodiments thereof with reference to the attached drawings in which.

DESCRIPTION OF THE PREFERRED EMBODIMENTS

Figure 2:
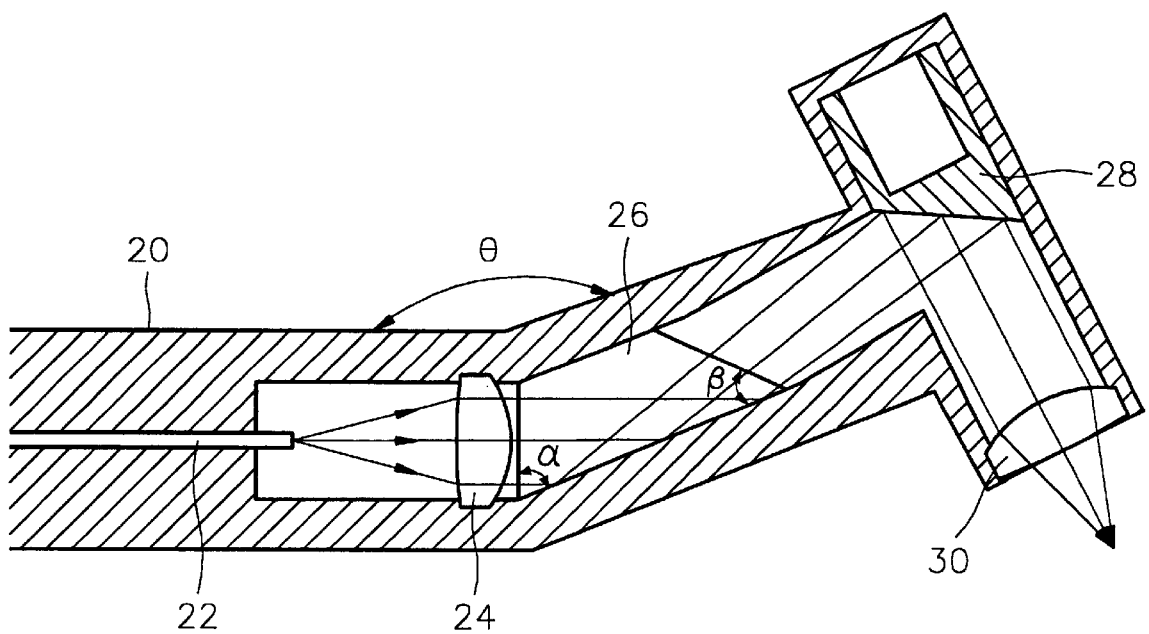
FIG. 2 shows a laser handpiece according to a first embodiment of the present invention.

Referring to FIG. 2, a laser handpiece according to a first embodiment of the present invention comprises a laser fiber 22 for irradiating a laser beam output from a laser generating device (not shown), a collimating lens 24 for collimating the laser beam irradiated from the laser fiber 22, a prism 26 for changing a traveling path of the laser beam output through the collimating lens 24, a reflective mirror 28 for finally changing the traveling path of the laser beam output through the prism 26, a focus lens 30 for focusing the laser beam reflected by the reflective mirror 28 on a point, and a main body 20 containing the laser fiber 22, the collimating lens 24, the prism 26, the reflective mirror 28 and the focus lens 30. Here, the collimating lens 24 and the prism 26 form a first beam path changing means, and the reflective mirror 28 is a second beam path changing means.

The prism 26 has two parallel reflective planes and two refractive planes. Preferably, the prism 26 is a Dove prism as shown in FIG. 2, in which the traveling path of laser beam is reflected at different angles according to the angles α and β between each reflective plane and each refractive planes.

In the laser handpiece according to the first embodiment of the present invention, the laser beam output from a laser generating device (not shown) are irradiated via the laser fiber 22, and the laser beam irradiated by the laser fiber 22 are collimated by the collimating lens 24 and then incident onto the prism 26, so that the traveling path of the laser beam is changed. Here, the prism 26 has two refractive planes and two reflective planes and changes the traveling path of the laser beam at its three plans, providing an effect of using three reflective mirrors to change the traveling path of the laser beam.

The traveling path of the laser beam the traveling path of which is changed by the prism 26 is finally changed by the reflective mirror 28 and then converged to a point by the focus lens 30.

In the above first embodiment of the present invention, the traveling path of the laser beam is changed using the prism 26 so that the size of the main body 20 does not become large even though the main body 20 is bent at an angle θ of 90° or over for convenience of use.

Figure 3:
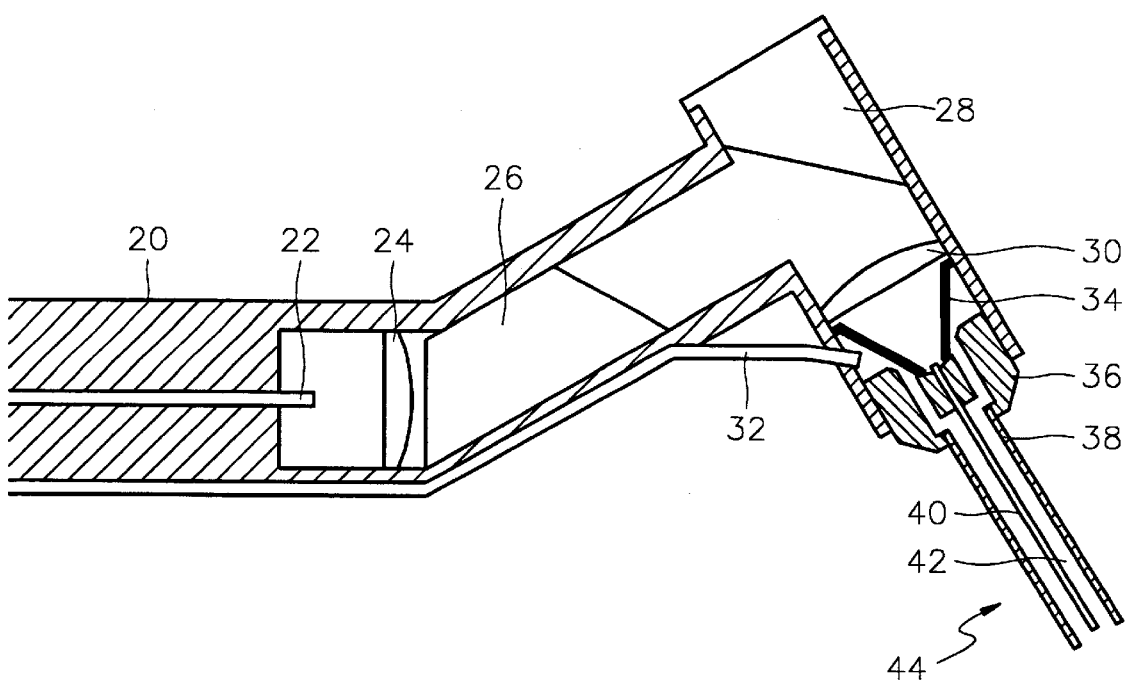
FIG. 3 shows a laser handpiece according to a second embodiment of the present invention.

FIG. 3 shows a laser handpiece according to a second embodiment of the present invention. The laser handpiece in FIG. 3, compared to the laser handpiece shown in FIG. 2, further comprises air and water supply tubes 32 for supplying air and water from the outside to clean and cool the irradiated portion (not shown) of the laser beam, and a light irradiating tip 44 having an injecting portion 42 for injecting the air and water supplied via the air and water supply tubes 32 onto the irradiated portion (not shown) and an optical fiber 40 as an energy transferring portion for transferring the energy of a laser beam converged by the focus lens 30 to the irradiated portion. In FIG. 3, reference numeral 36 represents a connecting portion that connects the main body 20 to the light irradiating tip 44, reference numeral 38 represents a protecting portion for protecting from damage to the optical fiber 40 by physical strength, and reference numeral 34 represents a blocking portion for blocking the laser beam converged by the focus lens 30 and incident onto the optical fiber 40 from the air and water supplied via the air and water supply tubes 32. The air and water supply tubes 32 is illustrated as a single tube in FIG. 3, however actually the air and water supply tubes 32 comprise two tubes one of which is for supplying air and the other of which is for supplying water.

Figure 4A:
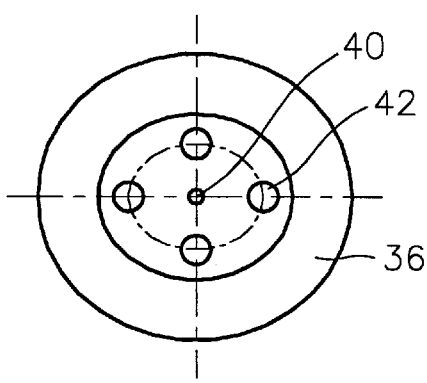
FIGS. 4A and 4B are a top view and a magnified view of the light radiating tip shown in FIG. 3.
Figure 4B:
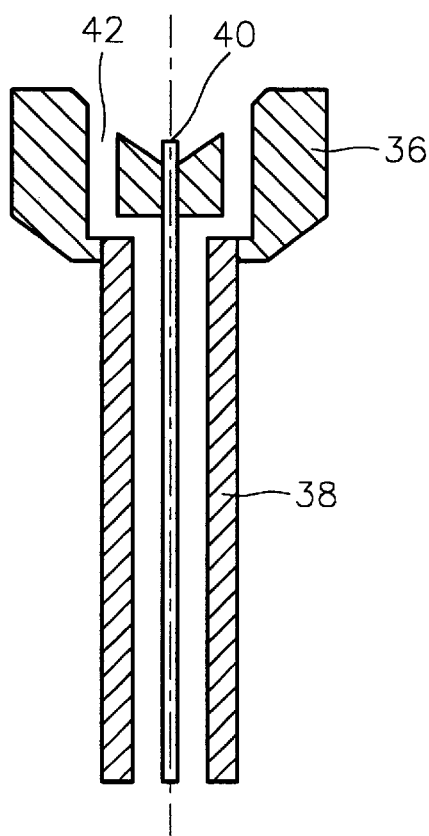

Meanwhile, FIGS. 4A and 4B are a top view and a magnified view of the light irradiating tip 44 of FIG. 3.

The laser handpiece of FIG. 3 comprises air and water supply tubes 32 and the light irradiating tip 44, so that it is easy to irradiate the laser beam onto a predetermined position of the irradiated portion, the irradiated portion can be cleaned and cooled, and the laser handpiece is endurable to damage due to a mechanical stresses, such as a hard subject such as teeth.

Figure 5A:
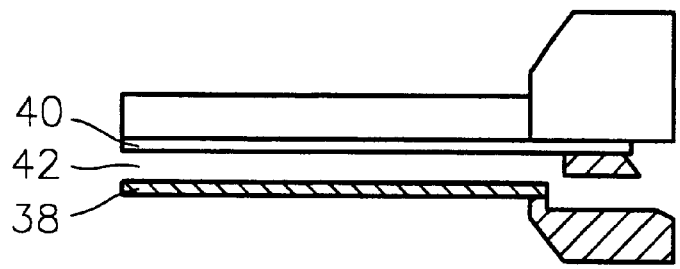
FIGS. 5A through 5C show various examples of the light radiating tip shown in FIG. 3.
Figure 5B:
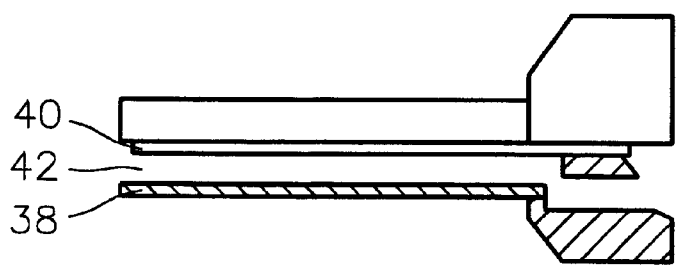
Figure 5C:
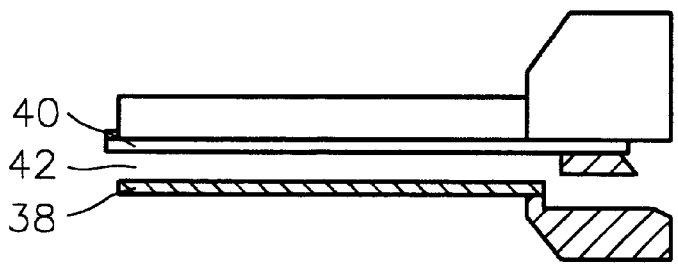

FIGS. 5A through 5C illustrate various examples of the light irradiating tip 44 shown in FIG. 3.

In the light irradiating tip shown in FIG. 5A, an end part of the optical fiber 40 and an end part of the protecting portion 38 end at the same end position such that the laser beam is output from the optical fiber 40 in the same direction as the air and water supply direction. In the light irradiating tip of FIG. 5B, the end part of the optical fiber is recessed compared to the end part of the protecting portion 38 in order to particularly protect the optical fiber 40. Also, in the light irradiating tip of FIG. 5C, the end part of the optical fiber 40 is formed to protrude compared to the end part of the protecting portion 38, such that the laser beam output from the optical fiber 40 is less affected by the air and water injected from the injecting portion 42.

Figure 6A:
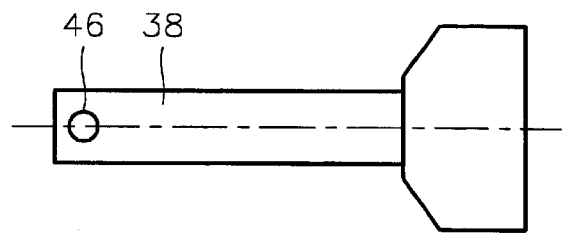
FIGS. 6A and 6B show examples of the light radiating tip having an additional injection hole.
Figure 6B:
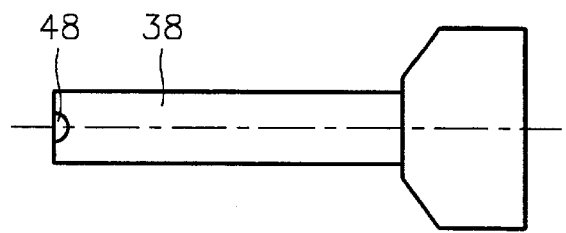

FIGS. 6A and 6B show examples of the light irradiating tip having an additional injecting hole. The light irradiating tip of FIG. 6A further comprises a circular injecting hole 46 at the end part of the protecting portion 38 so that air and water flow smoothly, and so that the air and water are efficiently injected into the irradiated portion. The light irradiating tip of FIG. 6B further comprises a semicircular injecting hole 48 at the end part of the protecting portion 38 so that air and water flow smoothly, and so that the air and water are efficiently injected into the irradiated portion.

Figure 7:
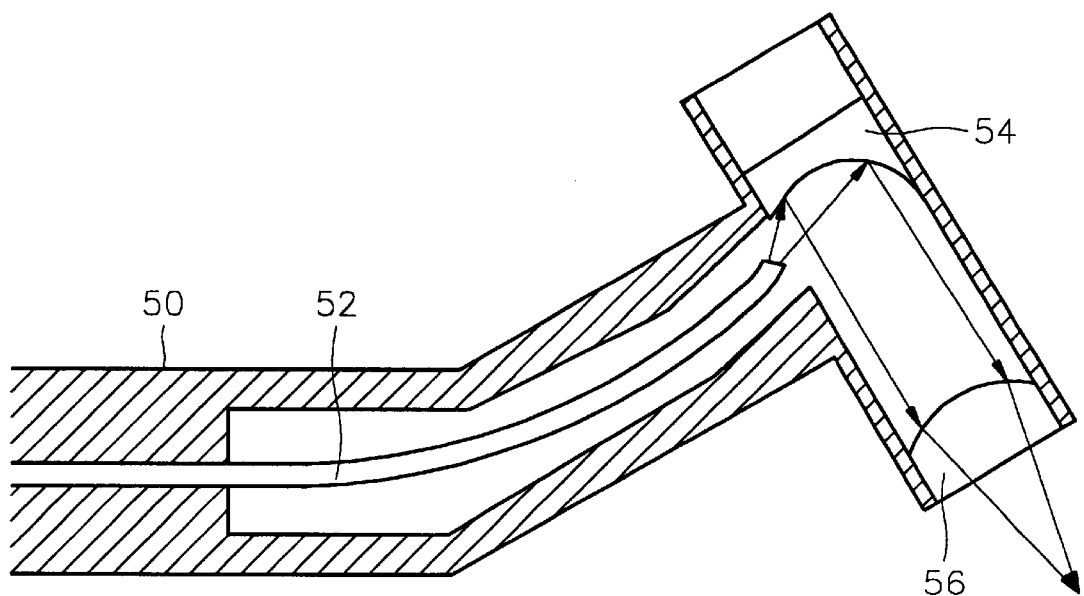
FIG. 7 shows a laser handpiece according to a third embodiment of the present invention.

FIG. 7 shows a laser handpiece according to a third embodiment of the present invention. The laser handpiece of FIG. 7 comprises a laser fiber 52 for irradiating a laser beam output from a laser generating device (not shown) by changing the direction of the laser beam, a concave reflective mirror 54 for finally changing the traveling path of the laser beam output from the optical fiber 52, a focus lens 56 for focusing the laser beam reflected by the concave reflective mirror 54 to a point, and a main body 50 containing the laser fiber 52, the concave reflective mirror 54 and the focus lens 56.

Figure 1:
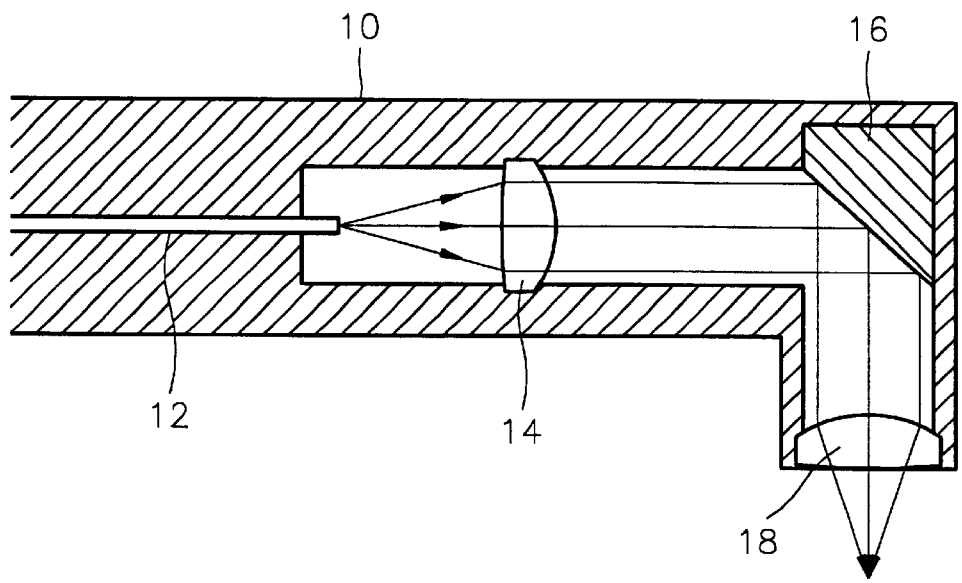
FIG. 1 shows a conventional laser handpiece.

In the third embodiment of the present invention, a laser fiber 52 extended from the laser fiber 22 at a predetermined angle is adopted instead of using the collimating lens 24 and the prism 26 as in the laser handpiece according to the first embodiment of FIG. 1, and a concave reflective mirror 54 is used instead of the reflective mirror 28 of FIG. 2. That is, the traveling path of the laser beam output from a laser generating device is directly changed using the laser fiber 52 and then output via the concave reflective mirror 54 to the focus lens 56. Thus, the traveling path of the laser beam can be easily changed within a small space.

The laser handpiece according to the third embodiment shown in FIG. 7 may further comprise air and water supply tubes and a light irradiating tip as in the second embodiment, and various types of light irradiating tips shown in FIGS. 5 and 6 can be adopted.

As described above, in the laser handpiece according to the present invention, a prism is adopted as a first beam path changing means so that an easy alignment of an optical axis can be achieved, or the traveling path of the laser beam can be easily changed within a small space by adopting a laser fiber as a first beam path changing means, thus a laser handpiece that is convenient to grip for use can be manufactured. Also, using the laser handpiece according to the present invention, lights having several different wavelengths such as aiming wavelength are irradiated onto a target region of an subject, as one point without aberration. Also, the laser handpiece according to the present invention can be applied to medical devices including dental and plastic lasers, etc., in addition to industrial devices using a laser.

What is claimed is:

1. A laser handpiece comprising:
   a laser fiber for emitting laser beam output from a laser generating device;
   a first beam path direction changing portion for changing direction of a traveling path of the laser beam output from the laser fiber;
   a second beam path direction changing portion for changing direction of the traveling path of the laser beam output from the first beam path changing portion;
   a focus lens for focusing the laser beam output from the second beam path changing portion onto a point; and
   a main body for containing the laser fiber, the first beam path changing portion, the second beam path changing portion and the focus lens.

2. The laser handpiece of claim 1, wherein the first beam path changing portion comprises:
   a collimating lens for collimating the laser beam emitted from the laser fiber; and
   one or more prisms for changing the traveling path of the laser beam output from the collimating lens.

3. The laser handpiece of claim 2, wherein the second beam path changing portion comprises a reflective mirror for finally changing the traveling path of the incident laser beam and outputting the reflected beam to the focus lens.

4. The laser handpiece of claim 2, wherein the prism of the first beam path changing portion is a Dove prism having two refractive planes and two parallel reflective planes.

5. The laser handpiece of claim 2, wherein the main body is bent at an angle of 90° or over for convenience of use.

6. The laser handpiece of claim 2, further comprising:
   air and water supply tubes for supplying air and water from the outside to clean and cool an irradiated portion being irradiated by the laser beam; and
   a light emitting tip having an injecting portion for injecting the air and water supplied via the air and water supply tubes into the irradiated portion, and an energy transferring portion for transferring the energy of the laser beam condensed by the focus lens to the irradiated portion.

7. The laser handpiece of claim 6, wherein the energy transferring portion is an optical fiber.

8. The laser handpiece of claim 6, wherein the light emitting tip further comprises:
   a connecting portion to be connected to the main body; and
   a protecting portion for protecting the energy transferring portion from damage by a physical force.

9. The laser handpiece of claim 8, wherein an end part of the energy transferring portion and an end part of the protecting portion end at the same end position.

10. The laser handpiece of claim 8, wherein an end part of the energy transferring portion is recessed compared to an end part of the protecting portion.

11. The laser handpiece of claim 8, wherein an end part of the energy transferring portion is formed to protrude compared to an end part of the protecting portion.

12. The laser handpiece of claim 9, wherein the protecting portion further comprises one or more injecting holes at the end part, for injecting the air and water into the irradiated portion.

13. The laser handpiece of claim 1, wherein the first beam path changing portion is formed by bending the laser fiber for emitting the laser beam output from the laser generating device at a predetermined angle such that an end part of the laser fiber emitting the laser beam is located near the second beam path changing portion, and the second beam path changing portion comprises a concave reflective mirror for changing the traveling path of the laser beam output from the laser fiber toward the focus lens.

14. The laser handpiece of claim 13, further comprising:
   air and water supply tubes for supplying air and water from the outside to clean and cool an irradiated portion being irradiated by the laser beam; and
   a light emitting tip having an injecting portion for injecting the air and water supplied via the air and water supply tubes into the irradiated portion, and an energy transferring portion for transferring the energy of the laser beam condensed by the focus lens to the irradiated portion.

15. The laser handpiece of claim 14, wherein the energy transferring portion is an optical fiber.

16. The laser handpiece of claim 14, wherein the light emitting tip further comprises:
   a connecting portion to be connected to the main body; and
   a protecting portion for protecting the energy transferring portion from damage by a physical force.

17. The laser handpiece of claim 16, wherein an end part of the energy transferring portion and an end part of the protecting portion end at the same end position.

18. The laser handpiece of claim 16, wherein an end part of the energy transferring portion is recessed compared to an end part of the protecting portion.

19. The laser handpiece of claim 16, wherein an end part of the energy transferring portion is formed to protrude compared to an end part of the protecting portion.

20. The laser handpiece of claim 16, wherein the protecting portion further comprises one or more injecting holes at the end part, for injecting the air and water into the irradiated portion.

* * * * *